United States Patent [19]

Ueno et al.

[11] Patent Number: 5,789,226
[45] Date of Patent: Aug. 4, 1998

[54] GENES ENCODING ENZYMES OF BALI RESTRICTION-MODIFICATION SYSTEM

[75] Inventors: Harumi Ueno, Kusatsu; Yoshizumi Ishino, Takatsuki; Ikunoshin Kato, Uji, all of Japan

[73] Assignee: Takara Shuzo Co., Ltd., Kyoto-fu, Japan

[21] Appl. No.: 595,559

[22] Filed: Feb. 1, 1996

[30] Foreign Application Priority Data

Feb. 3, 1995 [JP] Japan .................. 7-016812

[51] Int. Cl.⁶ .............. C12N 9/22; C12N 15/55
[52] U.S. Cl. ............ 435/199; 435/252.3; 435/320.1; 536/23.2
[58] Field of Search .............. 435/199, 220.1, 435/252.3, 252.33; 536/23.2

[56] References Cited

U.S. PATENT DOCUMENTS 5,200,333  4/1993  Wilson .................. 435/172.3
5,320,957  6/1994  Brooks et al. ............ 435/172.3

OTHER PUBLICATIONS

Geoffrey G. Wilson, Organization of Restriction–Modification Systems, Nucleic Acids Research, vol. 19 No. 10, pp. 2539–2565, 1991.
Geoffrey G. Wilson, Cloned–Restriction Systems—a Review, Gene, vol. 74, pp. 281–289, 1988.
R.E. Gelinas et al, A Specific Endonuclease from Brevibacterium Albidum, J.Mol. Biol., vol. 114, pp. 433–440, 1977.
Lunnen, K.D., et al. (1988) Gene 74, 25–32.
Ueno, H, et al (1996) Nucl. Acids Res. 24(12), 2268–2270.
Promega 1994–1995 Catalog, Biological Research Products (1994), p. 9.

Primary Examiner—Charles L. Patterson, Jr.
Attorney, Agent, or Firm—Browdy & Neimark

[57] ABSTRACT

An isolated BalI restriction enzyme gene and an BalI isolated modification enzyme gene are disclosed. A process for preparing a large amount of BalI restriction enzyme which comprises culturing a transformant containing said genes and collecting BalI restriction enzyme from the culture broth is also disclosed.

14 Claims, 3 Drawing Sheets

GENES ENCODING ENZYMES OF BALI RESTRICTION-MODIFICATION SYSTEM

FIELD OF THE INVENTION

The present invention relates to a restriction enzyme and a modification enzyme which are useful as reagents for genetic engineering. More particularly, the present invention relates to genes encoding enzymes of BalI restriction-modification system, and a genetic engineering process for preparing BalI restriction enzyme using them.

BACKGROUND OF THE INVENTION

BalI restriction and modification enzyme system is produced by *Brevibacterium albidum* ATCC 15831 (hereinafter called Bal strain), and composed of BalI restriction enzyme having a DNA cleaving activity and BalI modification enzyme (also called methylase or methyl transferase) which protects DNA from cleavage by BalI restriction enzyme. BalI restriction enzyme belongs to the typical type II restriction enzyme. This enzyme recognizes a sequence comprising six bases (5'-TGGCCA-3') having a structure of a dyad axis of rotation and cleaves between G and C of the recognition sequence to leave blunt ends (Gelinas et al., Journal of Molecular Biology, 114, 433–440 (1977)). On the other hand, BalI modifying enzyme has an action to introduce a methyl group into the fourth cytosine base (C) from 5' side of the recognition sequence, therefore this enzyme has a function to protect DNA from cleavage by BalI restriction enzyme.

A process to prepare BalI restriction enzyme is described in Gelinas et al. Journal of Molecular Biology, above cited. However, a small amount of BalI restriction enzyme is obtained from BalI strain, and it is difficult to produce a large amount of the enzyme. It is thought that BalI restriction enzyme gene is cloned and a large amount of BalI restriction enzyme will be produced by genetic engineering. In such a case both BalI restriction enzyme gene and BalI modification enzyme gene are required.

Wilson, Gene, 74, 281–289 (1988) describes the BalI modification enzyme gene as one of various modification enzymes cloned. However, there is no detailed description for identifying the BalI modification enzyme gene, such as definite methods for cloning it and the structure or the sequences of the gene cloned. In addition, there is no report for BalI restriction enzyme gene.

OBJECTS OF THE INVENTION

The main object of the present invention is to provide genes encoding enzymes of BalI restriction-modification system, and a process for preparing BalI restriction enzyme by creating novel microorganisms, especially *Escherichia coli*, in which a plasmid or plasmids are introduced, containing genes encoding enzymes of BalI restriction-modification system suitable for industrial production of BalI restriction enzyme.

This object as well as other objects and advantages of the present invention will become apparent to those skilled in the art from the following description with reference to the accompanying drawings.

SUMMARY OF THE INVENTION

Figure 1:
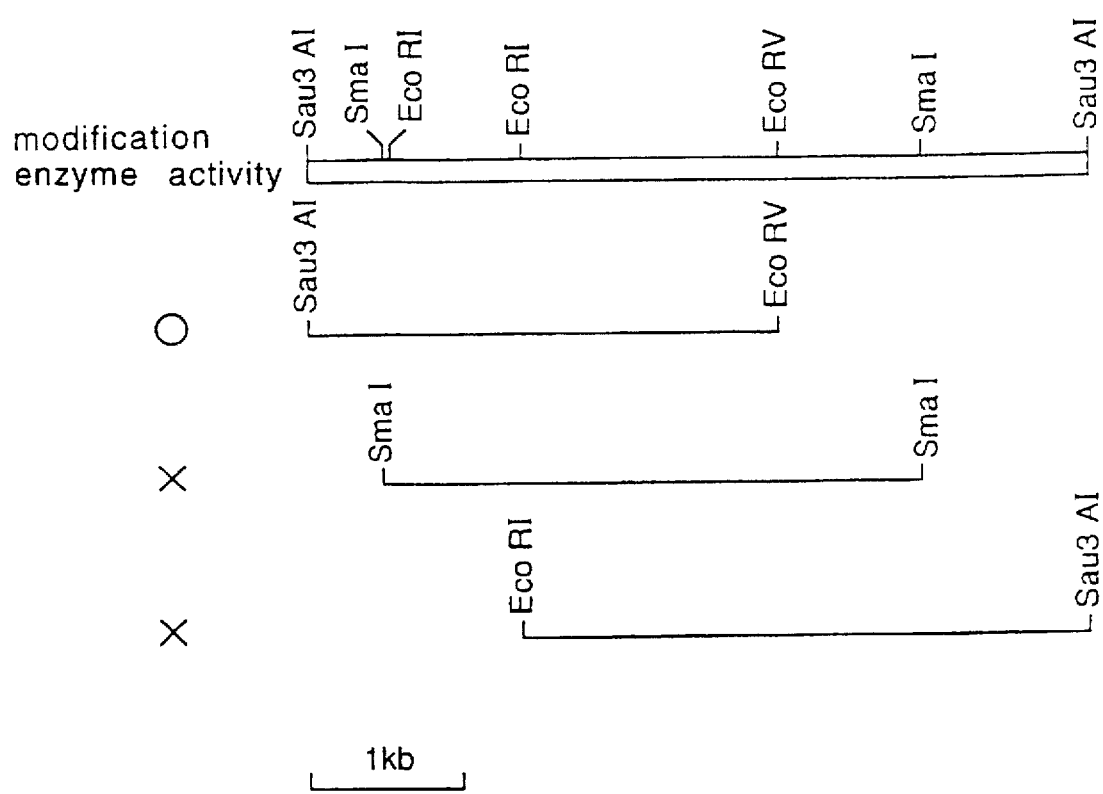
FIG. 1 shows a relation between each deletion mutant and the modification enzyme activity.

In the first aspect, the present invention relates to an isolated BalI restriction enzyme gene and a gene which can hybridize thereto. These genes have an equivalent function.

In the second aspect, the present invention relates to an isolated BalI modification enzyme gene and a gene which can hybridize thereto. These genes have an equivalent function.

In the third aspect, the present invention relates to a vector containing the gene of the first aspect.

In the fourth aspect, the present invention relates a vector containing the gene of the second aspect.

In the fifth aspect, the present invention relates to a vector containing the genes of both the first aspect and the second aspect.

In the sixth aspect, the present invention relates to a transformant transformed by both the vector of the third aspect and the vector of the fourth aspect, which can produce BalI restriction enzyme.

In the seventh aspect, the present invention relates to a transformant transformed by the vector of the fifth aspect, which can produce BalI restriction enzyme.

In the eighth aspect, the present invention relates to a process for preparing BalI restriction enzyme which comprises culturing the transformant of the sixth aspect or the seventh aspect, and collecting BalI restriction enzyme from the culture broth.

DETAILED DESCRIPTION OF THE INVENTION

The present inventors have studied intensively so as to succeed in cloning a DNA fragment containing genes encoding enzymes of BalI restriction-modification system from Bal strain. The present inventors also have found that a very large amount of BalI restriction enzyme is accumulated in cells and a large amount of the enzyme can be obtained from the culture broth by culturing a microorganism, especially *E. coli* carrying the single plasmid containing both restriction and modification enzymes genes or the plasmids containing these genes, individually.

A term "BalI restriction enzyme" used herein refers generically to polypeptides having BalI restriction enzyme activity.

A term "BalI modification enzyme" used herein refers generically to polypeptides having BalI modification enzyme activity.

Genes encoding enzymes of BalI restriction-modification system contain a gene encoding BalI restriction enzyme having an activity to cleave DNA and a gene encoding a modification enzyme which protects DNA from cleavage by BalI restriction enzyme. A term "genes encoding enzymes of restriction-modification system" means collectively a gene containing both restriction and modification enzyme genes, and individual genes thereof. In other words this term means restriction and/or modification enzyme gene. These genes can be used alone or in the form of a complex. When a plasmid(s) cloned both genes above mentioned is used, both genes can be cloned in the same plasmid, or these genes can be individually cloned in different plasmids.

In the present invention, for cloning genes encoding enzymes of restriction-modification system, a method called vector modifying method or methylase selection method is often used (Wilson, Gene, 74, 281–289 (1988)). This method is based on the prediction that the restriction enzyme gene and the modification enzyme gene locate in the vicinity each other. That is, some clones having modification enzyme activities should possess cognate restriction enzyme genes concurrently.

However, this method could not apply directly to cloning of genes encoding enzymes of BalI restriction-modification system.

That is, BalI restriction enzyme activity was not detected from clones having BalI modification enzyme activity. As a reason for this, for example, it was thought that BalI restriction enzyme gene did not locate in the vicinity of BalI modification enzyme gene, or that the full length of BalI restriction enzyme gene was not cloned although it located in the vicinity of BalI modification enzyme gene, or that it was not expressed in the host although the full length was cloned. In this point of time, it was impossible to expect which was the reason for that the candidate clone did not have restriction enzyme activity.

Wilson has been reported Multi-step cloning which is a developed method of methylase selection method in Gene above cited. However this method without modification cannot be applied when the gene can not be expressed in the host *E. coli* strain even if the full length is cloned while it is not expressed.

Consequently, it was found that BalI restriction enzyme gene was not expressed in *E. coli*, when the DNA fragment containing the gene was simply inserted into the plasmid vector. Therefore, the present inventors have constructed the expression system separately by determining the nucleotide sequence of whole BalI restriction enzyme gene and then altering the initiation region to ligate to the expression vector. Moreover, it was also found that appropriate cloning of genes encoding enzymes of BalI restriction-modification system depends on *E. coli* strain used.

Procedure for cloning and expression of BalI restriction and modifying system enzyme genes is shown below.

(1) Chromosomal DNA is extracted from Bal strain which is a DNA donor. The chromosomal DNA is partially digested with Sau3AI restriction enzyme and ligated to a vector having BalI recognition sequences.

(2) *E. coli* ER1648 is transformed by the plasmid library obtained in (1), and the plasmid library DNA is prepared by plasmid extraction method.

(3) The plasmid library DNA prepared in step (2) is digested with BalI restriction enzyme in vitro, where plasmids containing BalI modification enzyme gene that is expressed are not digested.

(4) *E. coli* ER1648 is again transformed by returning the plasmid library prepared in step (3), where only circular plasmids not digested are preferentially introduced into the host so that only transformants expressing BalI modification enzyme can be selected.

(5) BalI restriction enzyme activity is measured by an in vitro method for transformants obtained in step (4).

If BalI restriction enzyme activity is detected, BalI restriction enzyme gene exists in the clone and is expressed. Therefore the following steps (6)–(10) are not required. However, according to the present invention, BalI restriction enzyme activity was not detected and following steps were required.

(6) BalI restriction enzyme is purified as purely as possible from Bal strain according to the method of Gelinas above cited, and the amino acid sequence is determined from the amino terminal of the protein. In addition, the information for molecular weight is obtained by carrying out SDS-polyacrylamide gel electrophoresis (SDS-PAGE).

(7) Various deletion mutants are prepared from the clone of step (5) containing BalI modification enzyme gene, and location of BalI modification enzyme gene is identified.

(8) Whole nucleotide sequence of appropriate deletion mutants prepared in step (7). Then, the open reading frames (ORFs) are searched to predict BalI restriction enzyme gene and BalI modification enzyme gene from the informations obtained in steps (6) and (7).

(9) BalI restriction enzyme gene (not expressed in *E. coli*) is modified to be expressed, then ligated to an expression vector to construct an expression vector for BalI restriction enzyme gene.

(10) *E. coli* ER1648 is transformed by the vector containing BalI modification enzyme gene prepared in step (7) and the vector containing BalI restriction enzyme gene prepared in step (9) to create a transformant which can produce BalI restriction enzyme.

(11) The transformant obtained in step (10) is cultured and a large amount of BalI restriction enzyme is obtained.

As for vector used in step (1), a vector which contains BalI recognition sequence and the sequence of which is cleaved by BalI restriction enzyme can be used. The present inventors inserted BalI linker (5'-TTGGCCAA-3') into EcoRV site and NruI site of pBR322 to construct a vector in which BalI recognition sequences were newly introduced, and used it. The present inventors named this vector pBBB1.

The reason for introducing new BalI recognition sequences is that it was known that cleavage of BalI recognition sequence originally existing on pBR322 is difficult due to an effect of dcm methylase.

In transformation described in step (2), it was found according to the present inventors' experiment that stable transformants were not obtained depending on *E. coli* strain used. That is, stable transformants were obtained only when *E. coli* ER1648 was used. However a stable transformant is not obtained by use of strain HB101 or strain MC1061.

Therefore, strain ER1648 was used in the following steps.

The present inventors selected a plasmid containing an about 5.2 kb DNA fragment from Bal strain which contained BalI modification enzyme gene derived from the transformant obtained in steps (3)–(4). The plasmid was called pBB5.

In step (5), BalI restriction enzyme activity of the clones obtained is measured. BalI restriction enzyme activity can be measured by a in vitro method described below.

That is, the clone to be tested is cultured, and the culture broth are homogenized, then the supernatant from which debris is removed is obtained by ultracentrifugation. The enzyme reaction can be carried out at 37° C. using the supernatant as an enzyme fraction and lambda phage DNA as a substrate respectively. Analysis of the reaction products can be carried out by agarose gel electrophoresis. The present inventors investigated BalI restriction enzyme activity in the extract from *E. coli* ER1648 containing pBB5 to fail to detect the activity. As reasons for no activity, the three reason above mentioned were possible. However in this point of time, it was impossible to expect which reason was true. To decide this, the procedure described below was carried out.

In step (6), The amino acid sequence of the N-terminal of BalI restriction enzyme can be determined by transferring the purified BalI restriction enzyme to polyvinylydene difluoride (PVDF) membrane then using an automatic amino acid sequencer. The N-terminal amino acid sequence of BalI restriction enzyme determined by this method is shown in SEQ ID NO: 5. In addition, the molecular weight of BalI restriction enzyme was about 29,000 according to the result of SDS-PAGE.

Figure 2:
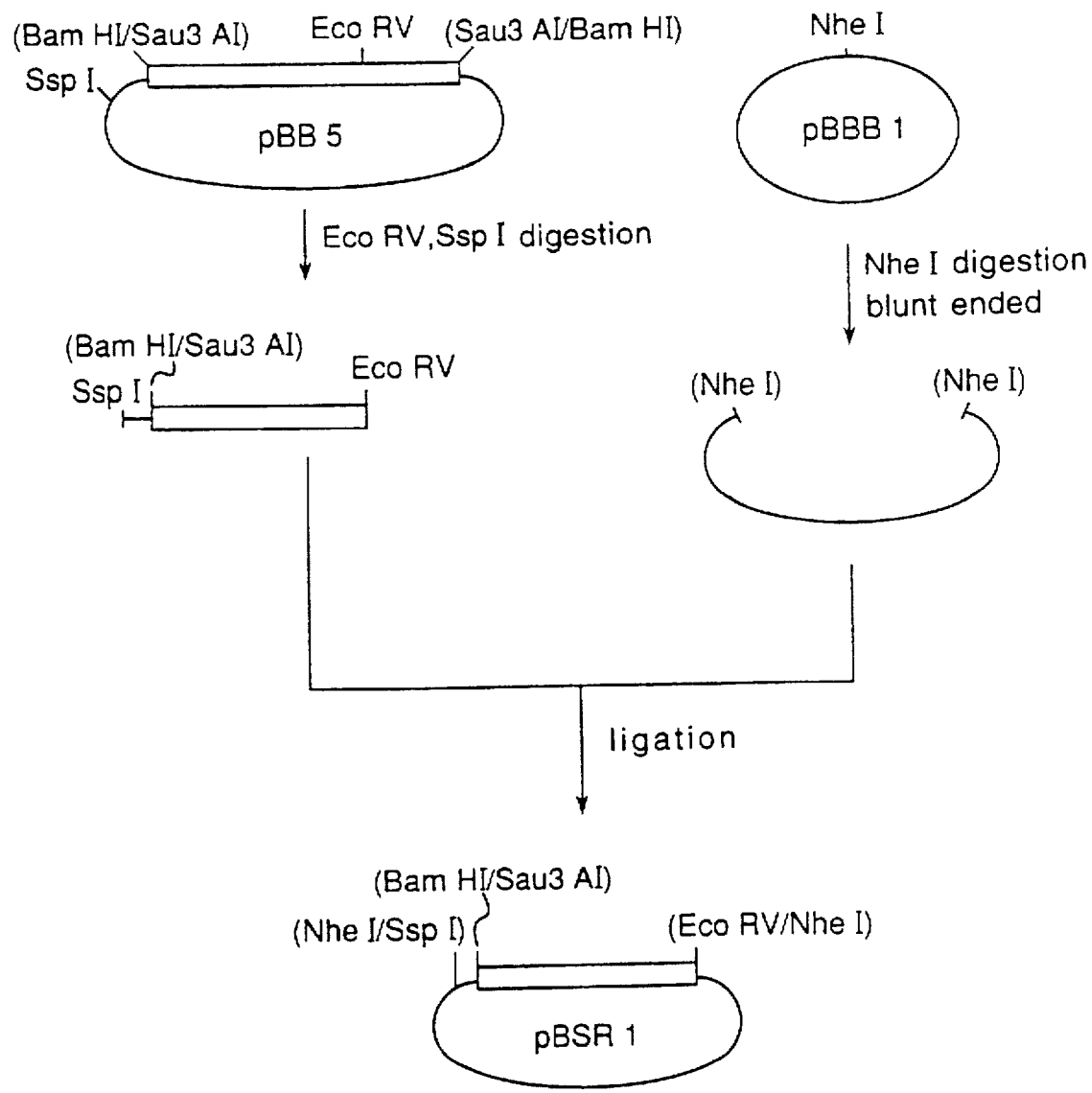
FIG. 2 shows a procedure for construction of pBSR1.

The relation between each deletion mutants prepared in step (7) and BalI modification enzyme activity is shown in FIG. 1. From the result it was found that BalI modification enzyme gene located on an about 3.2 kb DNA fragment. A plasmid prepared by inserting the DNA fragment into pBBB1, and named pBSR1. Procedure for construction of pBSR1 is shown in FIG. 2.

Figure 3:
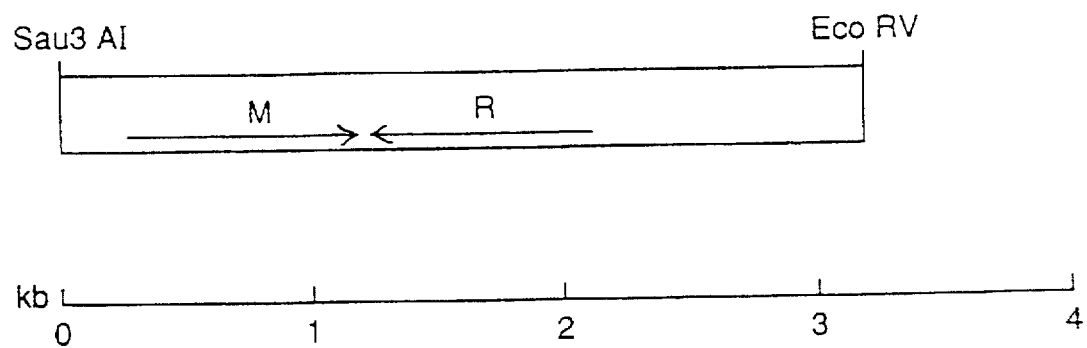
FIG. 3 shows the structure of BalI restriction and modification enzyme genes.

In step (8), whole nucleotide sequence of the 3.2 kb DNA fragment inserted into pBSR1 was determined. The sequence is shown in SEQ ID NO: 6. In addition, the ORFs were investigated and it was found that there were an ORF in normal direction (ORF1) in nucleotide 437–1276 and an ORF in reverse direction (ORF2) in nucleotide 1279–2058. The nucleotide sequence and the deduced amino acid sequence of ORF1 are shown in SEQ ID NO: 4. The amino acid sequence alone is shown in SEQ ID NO: 3. the nucleotide sequence and the deduced amino acid sequence of ORF2 are shown in SEQ ID NO: 2. The amino acid sequence alone is shown in SEQ ID NO: 1. From the relation between each deletion mutant prepared in step (7) and BalI modification enzyme activity, it was concluded that ORF1 encoded BalI modification enzyme. This was confirmed by the fact that E. coli, in which an expression vector cloned a DNA fragment obtained by PCR amplification of only ORF1 was introduced, possessed BalI modification enzyme activity. Also, it was decided that ORF2 encoded BalI restriction enzyme from the fact that the amino acid sequence of N-terminal obtained in step (6) coincided with that of ORF2. In addition, the molecular weight calculated from the amino acid sequence of SEQ ID NO: 1 was 29,043 which agreed well with the result of SDS-PAGE obtained in step (6). The structure of the cloned genes encoding enzymes of BalI restriction-modification system is shown in FIG. 3. In FIG. 3, M represents the modification enzyme gene, R represents the restriction enzyme gene, and arrows represent directions of ORFs.

Thus, the structure of the cloned genes encoding enzymes of BalI restriction-modification system was identified. It was found that BalI restriction enzyme gene was not expressed in E. coli although the whole part was cloned.

In step (9), the present inventors altered the initiation codon of ORF2, GTG into ATG, and also constructed an expression system for BalI restriction enzyme gene by ligating the gene to the downstream of the lac promoter acting strongly in E. coli. Firstly, ORF2 was PCR amplified. In this PCR amplification, the primer sequence was designed so that the initiation codon was ATG. Then, the amplified gene was ligated to downstream of lac promoter of pSTV28 vector (manufactured by Takara Shuzo Co.). The vector was named pSRB8. The transformant obtained by introducing pSRB8 and pBSR1 expressing BalI modification enzyme into E. coli ER1648 was designated as *Escherichia coli* ER1648/pBSR1/pSRB8, and has been deposited under the accession number FERM BP-5229 to National Institute of Bioscience and Human-Technology, Agency of Industrial Science and Technology, Ministry of International Trade and Industry.

In step (10), from 1 g of cultured *E. coli* ER1648/pBSR1/pSRB8 cells, about 70,000 units of BalI restriction enzyme activity was detected, which was about one hundred times as much as the amount of the enzyme produced by BalI strain. In purifying BalI restriction enzyme from the culture broth, the enzyme can be extracted by for example ultra sonic treatment and ultracentrifugation after harvesting the cells from the culture broth. Then, the enzyme can be purified by combination of removing nucleic acid, salting-out, affinity chromatography, gel filtration, ion exchange chromatography etc. By these method, a large amount of BalI restriction enzyme can be obtained.

Hybridization under a stringent condition is carried out using the gene obtained above as a probe so that similar genes coding similar enzyme activity can be obtained although the sequences are slightly different from that of the gene obtained above. These genes are also included within the present invention.

Such a stringent condition means the following hybridization condition wherein hybridization between the DNA fixed to a nylon membrane and the probe is carried out in a solution containing 6×SSC (1×SSC is prepared by dissolving NaCl 8.76 g and sodium citrate 4.41 g in 1 L water), 1% sodium lauryl sulfate, salmon sperm DNA 100 micrograms/ml, 5×Denhardt's (containing 0.1% bovine serum albumin, 0.1% polyvinyl pyrrolidone and 0.1% Ficoll), at 65° C. for 20 hours.

As for a method to obtain similar genes coding enzymes of BalI restriction-modification system by hybridization, for example the method described below is typical.

Firstly, chromosomal DNA obtained from selected gene source is ligated to a plasmid or phage vector, and introduced it into a host to make a library according to a conventional method. The library is cultured on plates, and colonies or plaques grown on the plates are transferred to nylon membranes. Then the DNA are fixed to the membranes by denaturation. Hybrids are formed between the DNA on the membranes and the probe previously labelled with for example $^{32}P$ by incubating the membrane in the solution containing the probe (Probe coding the genes for example shown in SEQ ID NO: 2 or SEQ ID NO: 4 or a portion thereof can be used). For example, a membrane to which the DNA is fixed is hybridized with the probe under the stringent condition.

After hybridization, non-specific adsorption is washed out, and clones forming hybrids with the probe are identified by for example autoradiography. This operation is repeated until the clone forming hybrid becomes single. The gene coding the objective protein is inserted in the clone obtained as above described.

The nucleotide sequence of the gene obtained is determined for example as follows. Then, it is confirmed whether the gene encodes the objective BalI restriction and modifying system enzymes.

In case of the clone obtained by hybridization, the nucleotide sequence was determined by culturing the transformant in a test tube and extracting the plasmid according to a conventional method (the transformant is E. coli). The plasmid is digested with appropriate restriction enzymes. The insert is taken out and subcloned into for example M13 phage vector, then the nucleotide sequence is determined by dideoxy method. When the recombinant is a phage, the nucleotide sequence can be determined by a substantially similar operation.

For these basic experiments from cultivation to determination of the nucleotide sequence, see for example T. Maniatis et al., Molecular Cloning A laboratory Manual, 1982, Cold Spring Harbor Laboratory.

To confirm whether the gene obtained encodes the objective BalI restriction and modification system enzymes or not, the nucleotide sequence determined above can be compared with the nucleotide sequence shown in SEQ ID NO:

2 or SEQ ID NO: 4 and the amino acid sequence shown in SEQ ID NO: 1 or SEQ ID NO: 3.

If the gene does not contain the whole region encoding BalI restriction and modifying system enzymes, the whole coding region can be obtained by a synthesizing DNA primers based on the gene obtained and PCR amplification of the lacked region, or by further screening the DNA library using the fragment of the gene obtained as a probe.

To obtain a polypeptide having BalI restriction or modification enzyme activity by genetic engineering, the gene of BalI restriction-modification system obtained is ligated to an expression vector which can expressed in for example *E. coli, Bacillus subtilis*, Actinomycetes, yeasts, animal cells, insect cells, and plant cells, according to a conventional method, then the connected vector is introduced into the host cell to obtain a transformant. A polypeptide having BalI restriction or modification system enzyme activity can be produced by culturing this transformant.

The polypeptide is sometimes accumulated as a insoluble material (inclusion body) depending on the expression system used. In this case, the polypeptide can be recovered by collecting the insoluble material and solubilizing it with a denaturing agent such as urea, then removing the denaturing agent. The expression can be confirmed by measuring BalI restriction enzyme activity or BalI modification enzyme activity. BalI restriction enzyme activity can be measured by the in vitro method above described, and BalI modification enzyme activity can be confirmed by that BalI recognition sequence of the DNA of the transformant is not digested with BalI restriction enzyme.

To purify the polypeptide having BalI restriction or modification enzyme activity from the transformant, chromatographic techniques similar to those above described can be used. When the expressed product is accumulated as an insoluble material, it can be solubilized as above described, for example by recovering the precipitation after disrupting the cells and solubilizing the precipitation with a denaturing agent such as urea. Then, after removing the denaturing agent and refolding, the polypeptide having the objective activity can be obtained by chromatographies above mentioned.

Also, in the present invention a transformant producing BalI restriction enzyme can be obtained by transforming the host by a vector containing both BalI restriction enzyme gene and BalI modification enzyme gene, which can be expressed. BalI restriction enzyme can be produced by culturing the transformant.

Such a vector can be obtained by for example preparing a vector which has been modified to express BalI restriction enzyme gene on pBSR1 in the host. As the reason for the fact that BalI restriction enzyme gene is not expressed in *E. coli*, it is thought, for example, that any promoter sequence suitable for transcription in *E. coli* does not exist upstream of the structural gene of the restriction enzyme, and that in *E. coli* the initiation codon for translation is GTG which is less effective. Therefore, the objective vector can be obtained by inserting a suitable promoter sequence into upstream of BalI restriction enzyme gene using in vitro genetic engineering method or by converting the initiation codon GTG into ATG using in vitro site-directed mutagenesis.

As shown in FIG. 3, the directions of transcription and translation of the restriction enzyme gene and the modification enzyme gene are opposed, and the end point of each gene are face each other so that it is possible that both genes interfere each other during the expression process. Therefore, the genes will be easily expressed by making the directions of both genes same. To carry out such a modification, for example, firstly a region containing the full length of the restriction enzyme gene and a region containing the full length of the modification enzyme gene are PCR amplified respectively. In this case, the primer sequences are designed so that suitable recognition sequences of the appropriate restriction enzymes can be used introduced into the termini of the amplified genes. Then, the objective vector can be obtained by ligating both genes in same direction using these sites and cloning them into an expression vector having a suitable promoter such as lac promoter.

Transformation of the host cell by these vectors, cultivation of the transformant obtained, and purification of the enzymes expressed can be also carried out as above described.

EXAMPLES

The following examples further illustrate the present invention in detail but not to be construed to limit the scope thereof.

Example 1
Preparation of chromosomal DNA from Bal strain

Bal strain was cultured in 100 ml of L broth (10 g/L tryptone, 5 g/L yeast extract, 5 g/L NaCl) at 37° C. overnight, then the cells were harvested by centrifugation. The cells were suspended in 10 ml of solution A (25 mM Tris-HCl (pH 8.0), 50 mM glucose, 10 mM EDTA). One ml of lysozyme solution (dissolved in solution A to be 2 mg/ml) was added and stirred, then the solution was stood for 15 min at 37° C. Then 28 ml of solution B (100 mM NaCl, 100 mM Tris-HCl (pH 8.0)) was added to the solution, and the mixture was stirred. 4 ml of 10% SDS solution was added, and the mixture was stirred and stood at 37° C. for 1 hour. 1 ml of solution C (10% SDS, 8% Sarcosyl) was added to the solution, and the mixture was stirred and stood at 60° C. for 15 min. After standing the solution, an equal volume of mixture of phenol:chloroform (1:1) was added. The mixture was stirred gently for 10 min, then aqueous layer and chloroform layer were separated by centrifugation (5000×g, 10 min). After separation, the aqueous layer was removed and an equal volume of isopropyl alcohol was added to it. The mixture was stirred and stood at 0° C. for 10 min, then the DNA was precipitated by centrifugation (13,500×g, 10 min). The precipitate was washed with 70% ethanol, dissolved in 10 ml of TE solution (10 mM Tris-HCl (pH 8.0), 1 mM EDTA) and stored at 4° C.

Example 2
Construction of cloning vector

A vector in which BalI linkers (5'-TTGGCCAA-3') (manufactured by Takara Shuzo Co.) were introduced in EcoRV restriction site and NruI restriction site of pBR322 was newly constructed as described below.

Firstly, 25 micrograms of pBR322 was digested with 150 units of EcoRV restriction enzyme in a buffer (10 mM Tris-HCl (pH 7.5), 7 mM MgCl$_2$, 150 mM NaCl, 7 mM 2-mercaptoethanol, 0.01% bovine serum albumin) at 37° C. for 1 hour and plasmid DNA was recovered by ethanol precipitation. This DNA was dissolved in 100 mM Tris-HCl (pH 8.0). 2.5 units of alkaline phosphatase (manufactured by Takara Shuzo Co.) was added and incubated at 55° C. for 1 hour. Then, phenol extraction and ethanol precipitation were carried out to recover the DNA. On the other hand, 5' terminal of 100 pmol of BalI linker was phosphorylated by use of 10 units of T4 polynucleotide kinase (manufactured by Takara Shuzo Co.) and the phosphorylated linker DNA was recovered by ethanol precipitation. 50 pmol of the phosphorylated BalI linker and 1 microgram of pBR322 DNA cleaved by EcoRV was ligated using 700 units of T4 DNA ligase (manufactured by Takara Shuzo Co.) in ligase buffer solution (66 mM Tris-HCl (pH 7.6), 6.6 mM dithiothreitol (DTT), 0.1 mM ATP) at 5° C. for 16 hours, then heated at 75° C. for 5 min and digested with 20 units of EcoRV. *E. coli* HB101 was transformed with the plasmid DNA thus obtained, and plated onto L broth agar containing 100 micrograms/ml of ampicillin. Colonies grown at 37° C. were isolated, and cultured in 2 ml of L broth at 37° C. for 16 hours, then the cell were harvested. The plasmid was isolated from the cells by alkali-SDS method.

That is, 0.2 ml of solution I (50 mM glucose, 10 mM Tris-HCl (pH 8.0), 5 mM EDTA) was added to the collected cells and the cells were suspended. 0.4 ml of solution II (0.2N NaOH, 1% SDS) was added and the mixture was maintained at 0° C. for 5 min. 0.3 ml of solution III (5M potassium acetate (pH 4.8)) was added to this mixture and the mixture was maintained at 0° C. for 15 min. Then the supernatant was removed by centrifugation. After adding 0.6 ml of isopropyl alcohol and maintaining the mixture at 0° C. for 10 min, the DNA was collected by centrifugation and the precipitation was washed with 70% ethanol. 0.1 ml of 20 micrograms/ml RNase was added to the precipitate and reacted at 37° C. for 40 min. 0.03 ml of 1M MgCl$_2$ was added and the mixture was maintained at 0° C. for 10 min. The supernatant was obtained by centrifugation and 0.06 ml of solution IV (20% polyethylene glycol #6000, 2M NaCl) was added to it. The mixture was stirred and maintained at 0° C. for 60 min. The precipitation was collected by centrifugation and dissolved in TE solution. This DNA solution was reacted with BalI restriction enzyme and agarose gel electrophoresis was carried out to select a plasmid containing BalI linker.

Then, the plasmid, in which BalI linker was inserted into the EcoRV site, was digested with NruI restriction enzyme to introduce BalI linker in the NruI site in a similar manner as above. Thus, a vector in which BalI linkers were introduced in EcoRV restriction site and NruI restriction site of pBR322 was obtained. The vector was named pBBB1.

Example 3
Preparation of library

Twenty-five micrograms of the chromosomal DNA obtained in Example 1 was partially digested with 1 unit of Sau3AI restriction enzyme in a buffer solution (50 mM Tris-HCl (pH 7.5), 10 mM MgCl$_2$, 1 mM DTT, 100 mM NaCl), and agarose gel electrophoresis was carried out to recover 3–7 kb DNA fragments. These DNA fragments were ligated to pBBB1 previously cleaved with BamHI, then *E. coli* ER1648 was transformed with these plasmids. Plasmids were extracted from the transformants thus obtained by alkali-SDS method to prepare a plasmid library.

Example 4
Isolation of modification enzyme gene

Three micrograms of the plasmid library prepared in Example 3 was reacted with 50 units of BalI restriction enzyme in a buffer solution (20 mM Tris-HCl (pH 8.5), 7 mM MgCl$_2$, 7 mM 2-mercaptoethanol, 0.01% bovine serum albumin). In this reaction, the plasmids expressing BalI modification enzyme were not cleaved with BalI restriction enzyme. After reaction, phenol extraction and ethanol precipitation were carried out to recover the DNA. Then, the DNA was dissolved in 100 mM Tris-HCl (pH 8.0). 2.5 units of alkaline phosphatase was added and reaction was carried out at 55° C. for 1 hour, then phenol extraction and ethanol precipitation were carried out to recover DNA again. *E. coli* ER1648 was transformed with the plasmids thus obtained which were cleaved or not cleaved. In this transformation, only circular plasmids not cleaved were preferentially introduced into the *E. coli* which could be selected as transformants on plates containing ampicillin. Thus, about 10,000 colonies were emerged and ten colonies were selected from them at random. Then, each colony was cultured in 2 ml of L broth containing 100 micrograms/ml of ampicillin at 37° C. for 16 hours, and the cells were collected. The plasmids were extracted by alkali-SDS method and treated with BalI restriction enzyme. Thus, three plasmids showed resistance to BalI restriction enzyme. Two plasmids of them lacked BalI sites itself on them, and only the remaining one expressed BalI modification enzyme gene. In this way, the transformant containing BalI modification enzyme gene was obtained. However, BalI restriction enzyme activity of this transformant was not found.

Example 5
Analysis of modification enzyme gene

The plasmid obtained in Example 4 which expressed BalI modification enzyme contained an about 5.2 kb DNA fragment from Bal strain. The plasmid was named pBB5. Then, to definite the location of BalI modification enzyme gene, a restriction map of the DNA fragment was made. Using this map, plasmids having DNA fragments in which various regions were deleted were prepared, and the modification enzyme activity expressed thereby was measured. Results are shown in FIG. 1. That is, it was found that BalI modification enzyme gene located on an about 3.2 kb DNA fragment. EcoRV-SspI fragment (3.7 kb) containing this about 3.2 kb fragment was cut out of pBB5, and ligated to pBBB1 to make a plasmid which was named pBSR1. Procedure of construction of pBSR1 is shown in FIG. 2.

Example 6
Determination of N-terminal amino acid sequence of BalI restriction enzyme BalI restriction enzyme was purified from Bal strain according to the method of Gelinas and subjected to SDS-PAGE, then transferred to PVDF membrane. Coomasie-brilliant blue staining was carried out and decolorization was carried out with 10% acetic acid-50% methanol. The area corresponding to MW 29,000 having BalI restriction enzyme was cut out and subjected to automatic Edman degradation by amino acid sequencer 470A (manufactured by Applied Biosystems) to determine the N-terminal amino acid sequence of the protein. The amino acid sequence is shown in SEQ ID NO: 5.

Example 7
Analysis of structure of genes encoding enzymes of BalI restriction-modification system The nucleotide sequence of the DNA fragment inserted into pBSR1 was determined by dideoxy chain-terminating method after preparing deletion mutants of various sizes using exonuclease III (manufactured by Takara Shuzo Co.) and mung bean nuclease (manufactured by Takara Shuzo Co.). The nucleotide sequence is shown in SEQ ID NO: 6. In addition, the ORFs were investigated so that it was found that an ORF in normal direction (ORF1) existed in nucleotide 437 to 1276 and an ORF in reverse direction (ORF2) existed in nucleotide 1279 to 2058. The nucleotide sequence of ORF1 and the deduced amino acid sequence are shown SEQ ID NO: 4 and the amino acid sequence alone is shown in SEQ ID NO: 3. The nucleotide sequence of ORF2 and the deduced amino acid sequence are shown SEQ ID NO: 2 and the amino acid sequence alone is shown in SEQ ID NO: 1. On the basis of the relation between each deletion mutant and BalI modification enzyme activity, it was concluded that ORF1 coded for BalI modification enzyme. It was concluded that ORF2 coded for BalI restriction enzyme because the N-terminal sequence coincided with that of ORF2. In addition, the molecular weight calculated from the amino acid sequence of SEQ ID NO: 1 was 29,043 which agreed well with the result of SDS-PAGE. The structure of cloned BalI restriction and modifying system genes is shown in FIG. 3. In this figure, M represents the modification enzyme gene, R represents the restriction enzyme gene, and arrows represent directions of ORFs.

Thus, the structure of genes encoding enzymes of BalI restriction-modification system was clarified. It was found that BalI restriction enzyme gene was not expressed in *E. coli* although the whole part was cloned.

Example 8
Construction of expression system for BalI restriction enzyme gene

A part of ORF2 was PCR amplified in 25 cycles (one cycle consisted of 94° C. for 1 min, 55° C. for 2 min, and 72° C. for 2 min), using BAL-R1 primer shown SEQ ID NO: 7 and BAL-2 primer shown in SEQ ID NO: 8 as a primer pair, and pBSR1 as a template. The initiation codon of the amplified gene was altered from GTG to ATG because the first base of BAL-1 primer was A. Then, the amplified DNA fragment was inserted into SmaI site of vector pSTV28 so that BalI restriction enzyme gene was located downstream of the lac promoter. The vector obtained was named pSRB8.

*E. coli* ER1648 was transformed with pBSR1 and pSRB8. BalI restriction enzyme activity in the extract of the obtained transformant was measured, and the activity was found. As above mentioned, this transformant was designated *Escherichia coli* ER1648/pBSR1/pSRB8 and deposited to National Institute of Bioscience and Human-Technology, Agency of Industrial Science and Technology, Ministry of International Trade and Industry (FERM BP-5229). Thus, a transformant expressing BalI restriction enzyme was obtained.

Example 9
Production of BalI restriction enzyme by transformant

*E. coli* ER1648/pBSR1/pSRB8 (FERM BP-5229) was inoculated to 100 ml of L broth containing 100 micrograms/ml of ampicillin and 30 micrograms/ml of chloramphenicol, and cultured at 37° C. for 5 hours. Then, IPTG was added to the final concentration 1 mM and further cultivation was carried out at 37° C. for 5 hours. One gram of cells were collected and suspended 5 ml of 20 mM Tris-HCl (pH 7.5) containing 10 mM 2-mercaptoethanol. The cells were disrupted by ultrasonic treatment and the supernatant was removed by ultracentrifugation (10,000 g, 30 min). The activity in the supernatant was measured and it was found that about 70,000 units of BalI restriction enzyme was produced per g cell. This activity was about one thousand as much as that obtained from Bal strain. As above mentioned, a system for mass-production of BalI restriction enzyme has been established.

As described hereinabove, according to the present invention, BalI restriction and modifying system genes are provided, and a large amount of BalI restriction enzyme which is important in genetic engineering can be produced efficiently.

What is claimed is:

1. An isolated BalI restriction enzyme gene.

2. A gene according to claim 1 which is obtainable from *Brevibacterium albidum* ATCC 15831.

3. A gene according to claim 1 which is obtainable from plasmid pSRB8.

4. A gene according to claim 1 which encodes an amino acid sequence shown in SEQ ID NO:1 or a portion thereof having BalI restriction enzyme activity.

5. A gene according to claim 1 comprising a nucleotide sequence selected from the group consisting of SEQ ID NO:2 and a portion thereof which encodes a polypeptide having BalI restriction enzyme activity.

6. A gene according to claim 1 comprising a nucleotide sequence selected from the group consisting of SEQ ID NO:2, wherein G at nucleotide position 1 is replaced by A, and a portion of the nucleotide sequence of SEQ ID NO:2 encoding a polypeptide having BalI restriction enzyme activity.

7. A gene according to claim 1 which is hybridizable to a gene having a nucleotide sequence shown in SEQ ID NO: 2 under a stringent condition.

8. A vector containing a gene according to claim 7.

9. A vector containing a gene according to claim 1.

10. A vector containing an isolated BalI restriction enzyme gene according to claim 1 and an isolated BalI modification enzyme gene selected from the group consisting of an isolated gene which is obtainable from plasmid pBSR1, an isolated gene which encodes an amino acid sequence of SEQ ID NO:3 or a portion thereof having BalI modification enzyme activity, an isolated gene comprising a nucleotide sequence of SEQ ID NO:4 or a portion thereof which encodes a polypeptide having BalI modification enzyme activity, and an isolated gene which is hybridizable to a gene having a nucleotide sequence of SEQ ID NO:4 under a stringent condition.

11. A transformant which can produce BalI restriction enzyme, transformed by a vector according to claim 2.

12. A transformant which can produce BalI restriction enzyme, transformed by a vector according to claim 8 and a vector selected from the group consisting of a vector containing an isolated BalI modification enzyme gene which is obtainable from plasmid pBSR1, a vector containing an isolated BalI modification enzyme gene which encodes an amino acid sequence shown in SEQ ID NO:3 or a portion thereof having BalI modification enzyme activity, and a vector containing an isolated BalI modification enzyme gene which is hybridizable to a gene having a nucleotide sequence of SEQ ID NO:4 under a stringent condition.

13. A process for preparing BalI restriction enzyme, comprising the steps of:

culturing a transformant according to claim 12 to express and accumulate BalI restriction enzyme; and recovering the accumulated BalI restriction enzyme.

14. A process for preparing BalI restriction enzyme, comprising the steps of:

culturing a transformant according to claim 11 to express and accumulate BalI restriction enzyme; and recovering the accumulated BalI restriction enzyme.

\* \* \* \* \*

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
  ( A ) LENGTH: 260
  ( B ) TYPE: amino acid
  ( C ) STRANDEDNESS: single
  ( D ) TOPOLOGY: linear ( x i ) SEQUENCE DESCRIPTION: SEQ ID NO: 1:

```
Met  Asp  Tyr  Ala  Phe  Arg  Asp  Arg  Pro  Leu  Asp  Asp  Val  Glu  Leu
 1              5                        10                       15

Glu  Val  Leu  Arg  Leu  Val  Leu  Ser  Ser  Phe  Arg  Asp  Gly  Ser  Gly
                     20                       25                       30

Gln  Val  Val  Arg  Pro  Asn  Gly  Gly  Thr  Met  Pro  Gly  Phe  Arg  Asp
                     35                       40                       45

Tyr  Glu  Arg  Gly  Leu  Ala  Ala  Val  Leu  His  Ala  Ser  Ala  Pro  Glu
                     50                       55                       60

Asn  Lys  Gly  Val  Phe  Asp  Val  Ile  Val  Pro  Val  Asp  Gly  Asp  Lys
                     65                       70                       75

Ser  Phe  Gly  Ile  Ser  Cys  Lys  Met  Ala  Thr  Thr  Pro  Pro  Ala  Lys
                     80                       85                       90

His  Ala  Ser  Ser  Phe  Met  Glu  Leu  Ser  Asn  Ser  Ala  Ala  Gln  Phe
                     95                      100                      105

Arg  Gln  Ala  Leu  Leu  Ala  Gln  Gln  Ile  Asn  Trp  Ala  Thr  Glu  Pro
                    110                      115                      120

Gly  Leu  Ala  Gly  Pro  Ala  Ile  Val  Arg  Leu  Val  Thr  Gly  Trp  His
                    125                      130                      135
```

| Asp | Ala | Thr | Ala | Asp<br>140 | Thr | His | Gln | Leu | Asp<br>145 | Leu | Pro | Ala | Ser | Lys<br>150 |
|-----|-----|-----|-----|-----|-----|-----|-----|-----|-----|-----|-----|-----|-----|-----|
| Tyr | Ser | Val | Leu | Ala<br>155 | His | Asn | Pro | Ser | Trp<br>160 | Thr | Gln | Phe | Gln | Leu<br>165 |
| Leu | Cys | Phe | Pro | Leu<br>170 | Asp | Leu | Gln | Ile | Ala<br>175 | Asn | Pro | Val | Gly | Glu<br>180 |
| Val | Glu | Trp | Leu | His<br>185 | Glu | Gly | Ala | Ser | Leu<br>190 | Asn | Gly | Tyr | Ile | Asp<br>195 |
| Asp | Gly | Gly | Arg | Arg<br>200 | His | Arg | Leu | Trp | Gln<br>205 | Cys | Tyr | Met | Asn | Ser<br>210 |
| Gly | Gly | Gln | Leu | Lys<br>215 | Tyr | Tyr | Pro | Leu | Leu<br>220 | Arg | Trp | Ala | Asp | Trp<br>225 |
| Val | Thr | Glu | Pro | Phe<br>230 | Thr | Leu | Glu | Leu | Pro<br>235 | Pro | Val | Ala | Ser | Pro<br>240 |
| Ile | Leu | Arg | Ala | Arg<br>245 | Asp | Tyr | Phe | Asn | Glu<br>250 | Val | Trp | Pro | His | Gly<br>255 |
| Trp | Asp | Asp | Arg | Asn<br>260 | | | | | | | | | | |

( 2 ) INFORMATION FOR SEQ ID NO: 2:

( i ) SEQUENCE CHARACTERISTICS:
        ( A ) LENGTH: 780
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO: 2:

```
GTG  GAT  TAC  GCG  TTT  CGT  GAC  CGG  CCG  CTC  GAC  GAT  GTC  GAG  CTG        45
Met  Asp  Tyr  Ala  Phe  Arg  Asp  Arg  Pro  Leu  Asp  Asp  Val  Glu  Leu
 1              5                        10                       15

GAG  GTC  CTC  CGG  CTG  GTA  TTG  AGC  TCG  TTC  CGA  GAC  GGA  TCC  GGT        90
Glu  Val  Leu  Arg  Leu  Val  Leu  Ser  Ser  Phe  Arg  Asp  Gly  Ser  Gly
                 20                       25                       30

CAG  GTT  GTC  CGC  CCC  AAT  GGC  GGC  ACA  ATG  CCA  GGC  TTC  CGC  GAC       135
Gln  Val  Val  Arg  Pro  Asn  Gly  Gly  Thr  Met  Pro  Gly  Phe  Arg  Asp
                 35                       40                       45

TAC  GAG  CGT  GGT  CTC  GCC  GCC  GTG  CTG  CAT  GCG  TCA  GCT  CCG  GAG       180
Tyr  Glu  Arg  Gly  Leu  Ala  Ala  Val  Leu  His  Ala  Ser  Ala  Pro  Glu
                 50                       55                       60

AAC  AAG  GGC  GTC  TTC  GAC  GTC  ATC  GTG  CCC  GTC  GAC  GGC  GAT  AAG       225
Asn  Lys  Gly  Val  Phe  Asp  Val  Ile  Val  Pro  Val  Asp  Gly  Asp  Lys
                 65                       70                       75

TCG  TTC  GGG  ATC  TCC  TGC  AAA  ATG  GCC  ACG  ACA  CCT  CCG  GCG  AAG       270
Ser  Phe  Gly  Ile  Ser  Cys  Lys  Met  Ala  Thr  Thr  Pro  Pro  Ala  Lys
                 80                       85                       90

CAT  GCG  TCG  AGT  TTC  ATG  GAG  CTG  TCT  AAC  TCC  GCC  GCC  CAG  TTC       315
His  Ala  Ser  Ser  Phe  Met  Glu  Leu  Ser  Asn  Ser  Ala  Ala  Gln  Phe
                 95                      100                      105

CGC  CAG  GCG  CTG  CTG  GCG  CAG  CAG  ATC  AAT  TGG  GCG  ACC  GAG  CCC       360
Arg  Gln  Ala  Leu  Leu  Ala  Gln  Gln  Ile  Asn  Trp  Ala  Thr  Glu  Pro
                110                      115                      120

GGT  CTT  GCT  GGC  CCT  GCG  ATC  GTG  CGT  CTG  GTT  ACC  GGT  TGG  CAC       405
Gly  Leu  Ala  Gly  Pro  Ala  Ile  Val  Arg  Leu  Val  Thr  Gly  Trp  His
                125                      130                      135

GAC  GCC  ACC  GCC  GAC  ACC  CAT  CAA  CTC  GAC  CTG  CCC  GCG  AGT  AAG       450
Asp  Ala  Thr  Ala  Asp  Thr  His  Gln  Leu  Asp  Leu  Pro  Ala  Ser  Lys
                140                      145                      150
```

| | | | | | | | | | | | | | | | |
|---|---|---|---|---|---|---|---|---|---|---|---|---|---|---|---|
| TAC | TCG | GTG | TTG | GCC | CAC | AAT | CCG | TCA | TGG | ACG | CAG | TTT | CAG | CTG | 495 |
| Tyr | Ser | Val | Leu | Ala 155 | His | Asn | Pro | Ser | Trp 160 | Thr | Gln | Phe | Gln | Leu 165 | |
| CTC | TGC | TTC | CCC | CTG | GAC | TTG | CAG | ATC | GCG | AAC | CCG | GTG | GGC | GAG | 540 |
| Leu | Cys | Phe | Pro | Leu 170 | Asp | Leu | Gln | Ile | Ala 175 | Asn | Pro | Val | Gly | Glu 180 | |
| GTG | GAG | TGG | CTG | CAC | GAG | GGT | GCT | TCG | CTG | AAC | GGG | TAT | ATC | GAT | 585 |
| Val | Glu | Trp | Leu | His 185 | Glu | Gly | Ala | Ser | Leu 190 | Asn | Gly | Tyr | Ile | Asp 195 | |
| GAC | GGC | GGC | CGA | CGG | CAT | CGG | TTG | TGG | CAG | TGC | TAC | ATG | AAT | TCC | 630 |
| Asp | Gly | Gly | Arg | Arg 200 | His | Arg | Leu | Trp | Gln 205 | Cys | Tyr | Met | Asn | Ser 210 | |
| GGC | GGG | CAG | CTG | AAG | TAC | TAC | CCG | CTG | TTG | CGG | TGG | GCG | GAC | TGG | 675 |
| Gly | Gly | Gln | Leu | Lys 215 | Tyr | Tyr | Pro | Leu | Leu 220 | Arg | Trp | Ala | Asp | Trp 225 | |
| GTG | ACG | GAG | CCG | TTC | ACG | CTG | GAA | CTG | CCG | CCG | GTG | GCG | TCA | CCG | 720 |
| Val | Thr | Glu | Pro | Phe 230 | Thr | Leu | Glu | Leu | Pro 235 | Pro | Val | Ala | Ser | Pro 240 | |
| ATC | CTC | CGG | GCC | CGT | GAC | TAC | TTC | AAC | GAG | GTC | TGG | CCG | CAC | GGT | 765 |
| Ile | Leu | Arg | Ala | Arg 245 | Asp | Tyr | Phe | Asn | Glu 250 | Val | Trp | Pro | His | Gly 255 | |
| TGG | GAC | GAC | CGT | AAC | | | | | | | | | | | 780 |
| Trp | Asp | Asp | Arg | Asn 260 | | | | | | | | | | | |

(2) INFORMATION FOR SEQ ID NO: 3:

(i) SEQUENCE CHARACTERISTICS:
        (A) LENGTH: 280
        (B) TYPE: amino acid
        (C) STRANDEDNESS: single
        (D) TOPOLOGY: linear (xi) SEQUENCE DESCRIPTION: SEQ ID NO: 3:

| | | | | | | | | | | | | | | |
|---|---|---|---|---|---|---|---|---|---|---|---|---|---|---|
| Met 1 | Thr | Leu | Glu | Gln 5 | Ile | Ser | Ala | Ala | Leu 10 | Arg | Thr | Glu | Arg | Val 15 |
| Pro | Ala | Ser | Ser | Asp 20 | Val | Pro | Trp | Ala | Ala 25 | Pro | Asn | Ala | Ala | Val 30 |
| Met | Arg | Tyr | Pro | Gly 35 | Ser | Lys | Trp | Ser | Leu 40 | Ala | Arg | Gln | Ile | Val 45 |
| Ala | Glu | Phe | Asp | Asp 50 | His | Tyr | His | Tyr | Val 55 | Glu | Pro | Phe | Phe | Gly 60 |
| Ser | Gly | Ala | Val | Phe 65 | Phe | Ser | Lys | Pro | Pro 70 | Val | Pro | His | Glu | Ile 75 |
| Leu | Asn | Asp | Thr | Asn 80 | Gly | Gln | Val | Val | Asn 85 | Leu | Phe | Arg | Val | Leu 90 |
| Arg | Asp | Arg | Thr | Glu 95 | Asp | Leu | Val | Trp | Gln 100 | Leu | Glu | Ala | Thr | Pro 105 |
| Trp | Ser | Arg | Asp | Glu 110 | Tyr | Asp | Arg | Ser | His 115 | Val | Leu | Thr | Gly | Asp 120 |
| Asp | Val | Glu | Asp | Ala 125 | Arg | Arg | Phe | Val | Val 130 | Arg | Cys | Trp | Gln | Ala 135 |
| His | Ala | Ser | Asp | Leu 140 | Ala | Lys | Lys | Thr | Gly 145 | Trp | Lys | Thr | Arg | Gly 150 |
| Ala | Gln | Gln | Arg | Ala 155 | Gly | Gly | Met | Ser | Leu 160 | Arg | Trp | Gln | Lys | Val 165 |
| Pro | Ala | Gln | Leu | Arg 170 | Glu | Leu | Ala | Trp | Arg 175 | Leu | Leu | Asp | Ala | Glu 180 |

| | | | | | | | | | | | | | |
|---|---|---|---|---|---|---|---|---|---|---|---|---|---|
|Ile|Glu|Asn|Arg|Asp|Ala|Val|Gln|Val|Ile|Arg|Arg|His|Asn|Ala|
| | | | |185| | | |190| | | | |195|
|Glu|Asn|Ala|Leu|Ile|Tyr|Ala|Asp|Pro|Pro|Tyr|Leu|His|Ser|Val|
| | | | |200| | | |205| | | | |210|
|Arg|Thr|Gln|Arg|Met|Tyr|Gly|Glu|Glu|Met|Thr|Asp|Thr|Glu|His|
| | | | |215| | | |220| | | | |225|
|Ile|Ala|Leu|Leu|Asp|Ala|Leu|Leu|Ala|His|Lys|Gly|Pro|Val|Val|
| | | | |230| | | |235| | | | |240|
|Val|Ser|Gly|Tyr|Ala|Asn|Asp|Leu|Tyr|Asp|Thr|Ala|Leu|Glu|Gly|
| | | | |245| | | |250| | | | |255|
|Trp|Arg|Lys|Val|Thr|Met|Lys|Ala|Pro|Lys|Val|Glu|Lys|Gly|Ala|
| | | | |260| | | |265| | | | |270|
|Ala|Arg|Thr|Glu|Val|Leu|Trp|Val|Lys|Arg| | | | | |
| | | | |275| | | |280| | | | | | |

( 2 ) INFORMATION FOR SEQ ID NO: 4:

( i ) SEQUENCE CHARACTERISTICS:
        ( A ) LENGTH: 840
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO: 4:

```
ATG ACG CTC GAG CAG ATC AGC GCG GCT CTA CGC ACG GAG CGG GTC      45
Met Thr Leu Glu Gln Ile Ser Ala Ala Leu Arg Thr Glu Arg Val
 1               5                  10                  15

CCG GCA TCT TCA GAC GTC CCA TGG GCG GCG CCG AAT GCT GCA GTG      90
Pro Ala Ser Ser Asp Val Pro Trp Ala Ala Pro Asn Ala Ala Val
                20                  25                  30

ATG CGC TAC CCG GGG TCG AAG TGG TCC CTC GCT CGG CAG ATT GTC     135
Met Arg Tyr Pro Gly Ser Lys Trp Ser Leu Ala Arg Gln Ile Val
                35                  40                  45

GCG GAA TTC GAT GAC CAC TAC CAC TAC GTG GAA CCG TTC TTC GGT     180
Ala Glu Phe Asp Asp His Tyr His Tyr Val Glu Pro Phe Phe Gly
                50                  55                  60

TCG GGG GCG GTG TTC TTC AGC AAG CCG CCG GTG CCG CAC GAG ATC     225
Ser Gly Ala Val Phe Phe Ser Lys Pro Pro Val Pro His Glu Ile
                65                  70                  75

CTC AAC GAC ACC AAC GGT CAG GTC GTG AAC CTG TTC CGG GTG CTT     270
Leu Asn Asp Thr Asn Gly Gln Val Val Asn Leu Phe Arg Val Leu
                80                  85                  90

CGC GAT CGG ACC GAG GAT CTG GTG TGG CAG CTT GAG GCG ACG CCT     315
Arg Asp Arg Thr Glu Asp Leu Val Trp Gln Leu Glu Ala Thr Pro
                95                 100                 105

TGG TCT CGG GAC GAG TAT GAC CGG TCG CAC GTC CTG ACC GGG GAT     360
Trp Ser Arg Asp Glu Tyr Asp Arg Ser His Val Leu Thr Gly Asp
               110                 115                 120

GAT GTC GAG GAC GCC AGA CGG TTC GTG GTT CGG TGC TGG CAG GCG     405
Asp Val Glu Asp Ala Arg Arg Phe Val Val Arg Cys Trp Gln Ala
               125                 130                 135

CAC GCG AGC GAC CTG GCG AAG AAG ACT GGG TGG AAG ACC CGC GGC     450
His Ala Ser Asp Leu Ala Lys Lys Thr Gly Trp Lys Thr Arg Gly
               140                 145                 150

GCG CAG CAG CGT GCC GGC GGG ATG TCG CTG CGG TGG CAG AAG GTG     495
Ala Gln Gln Arg Ala Gly Gly Met Ser Leu Arg Trp Gln Lys Val
               155                 160                 165

CCG GCG CAG CTG CGG GAG CTT GCC TGG CGG CTG TTG GAT GCG GAA     540
Pro Ala Gln Leu Arg Glu Leu Ala Trp Arg Leu Leu Asp Ala Glu
```

|     |     |     |     |     |     |     |     |     |     |     |     |     |     |     |
| --- | --- | --- | --- | --- | --- | --- | --- | --- | --- | --- | --- | --- | --- | --- |
|     |     |     |     | 170 |     |     |     |     | 175 |     |     |     | 180 |     |
| ATC | GAG | AAC | CGT | GAC | GCG | GTG | CAA | GTG | ATC | CGC | CGG | CAC | AAC | GCC | 585 |
| Ile | Glu | Asn | Arg | Asp | Ala | Val | Gln | Val | Ile | Arg | Arg | His | Asn | Ala |     |
|     |     |     |     | 185 |     |     |     |     | 190 |     |     |     | 195 |     |
| GAG | AAC | GCT | CTG | ATC | TAC | GCA | GAC | CCG | CCG | TAT | CTA | CAC | AGC | GTC | 630 |
| Glu | Asn | Ala | Leu | Ile | Tyr | Ala | Asp | Pro | Pro | Tyr | Leu | His | Ser | Val |     |
|     |     |     |     | 200 |     |     |     |     | 205 |     |     |     | 210 |     |
| CGC | ACG | CAG | CGC | ATG | TAC | GGC | GAG | GAG | ATG | ACC | GAC | ACC | GAG | CAC | 675 |
| Arg | Thr | Gln | Arg | Met | Tyr | Gly | Glu | Glu | Met | Thr | Asp | Thr | Glu | His |     |
|     |     |     |     | 215 |     |     |     |     | 220 |     |     |     | 225 |     |
| ATC | GCC | CTG | CTG | GAC | GCG | CTA | CTG | GCC | CAC | AAG | GGG | CCG | GTG | GTG | 720 |
| Ile | Ala | Leu | Leu | Asp | Ala | Leu | Leu | Ala | His | Lys | Gly | Pro | Val | Val |     |
|     |     |     |     | 230 |     |     |     |     | 235 |     |     |     | 240 |     |
| GTC | AGC | GGG | TAC | GCC | AAC | GAC | CTA | TAC | GAC | ACT | GCG | CTC | GAG | GGG | 765 |
| Val | Ser | Gly | Tyr | Ala | Asn | Asp | Leu | Tyr | Asp | Thr | Ala | Leu | Glu | Gly |     |
|     |     |     |     | 245 |     |     |     |     | 250 |     |     |     | 255 |     |
| TGG | CGC | AAG | GTG | ACA | ATG | AAG | GCG | CCG | AAG | GTC | GAG | AAG | GGT | GCC | 810 |
| Trp | Arg | Lys | Val | Thr | Met | Lys | Ala | Pro | Lys | Val | Glu | Lys | Gly | Ala |     |
|     |     |     |     | 260 |     |     |     |     | 265 |     |     |     | 270 |     |
| GCC | CGT | ACT | GAG | GTG | CTG | TGG | GTA | AAG | CGC |     |     |     |     |     | 840 |
| Ala | Arg | Thr | Glu | Val | Leu | Trp | Val | Lys | Arg |     |     |     |     |     |     |
|     |     |     |     | 275 |     |     |     |     | 280 |     |     |     |     |     |

( 2 ) INFORMATION FOR SEQ ID NO: 5:

( i ) SEQUENCE CHARACTERISTICS:
        ( A ) LENGTH: 26
        ( B ) TYPE: amino acid
        ( C ) STRANDEDNESS: single
        ( D ) TOPOLOGY: linear ( i x ) FEATURE:
        Xaa at position 1 is an unknown amino acid.
        Xaa at position 6 is an unknown amino acid.
        Xaa at position 24 is an unknown amino acid.

( x i ) SEQUENCE DESCRIPTION: SEQ ID NO: 5:

| Xaa | Asp | Tyr | Ala | Phe | Xaa | Asp | Arg | Pro | Leu | Asp | Asp | Val | Glu | Leu |
| --- | --- | --- | --- | --- | --- | --- | --- | --- | --- | --- | --- | --- | --- | --- |
| 1   |     |     |     | 5   |     |     |     |     | 10  |     |     |     |     | 15  |
| Glu | Val | Leu | Arg | Leu | Val | Leu | Ser | Xaa | Phe | Arg |     |     |     |     |
|     |     |     | 20  |     |     |     |     | 25  |     |     |     |     |     |     |

( 2 ) INFORMATION FOR SEQ ID NO: 6:

( i ) SEQUENCE CHARACTERISTICS:
        ( A ) LENGTH: 3182
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO: 6:

| GATCGTCACA | AACCGAGGGT | GGTCGTCGCC | ATCGACACGC | CGGTCGGAGT | GTCCCGCGGA | 60  |
| --- | --- | --- | --- | --- | --- | --- |
| CGGTACCGCC | TGTTACGGTA | CCGGTTATGG | GACATCAGGG | GCAGCACGTG | CCGCAGGCGG | 120 |
| TGCGTTGGGC | GCAGAAAGCG | CGTGAGGTGG | AGGCGTTCAC | CTCCGAATAC | ATCGAGTACC | 180 |
| TGCAGGCGCA | GCTGGTCAAG | CATGCCCTGC | ACGCCACTGG | TGCAAGTCAG | CGTGAGCTCG | 240 |
| CGGAGGACCT | CGGGACGAGT | AAGTCCCGGA | TCAATCGTCT | CGCGCGAGCG | TCCTCGGAGC | 300 |
| CGCCGCATGC | TGCGGAGACT | GAGGACGTCG | CAGCAGCGTT | GGAGACGATC | TTCCTCGGTA | 360 |
| CCCGCGTCAC | CGAGGTGCGG | GAGGGTGCTG | CTGCCTACGA | CCAGGCATCG | TCGGTGGCAG | 420 |
| CTGGGACGGT | GACCCGATGA | CGCTCGAGCA | GATCAGCGCG | GCTCTACGCA | CGGAGCGGGT | 480 |

```
CCCGGCATCT TCAGACGTCC CATGGGCGGC GCCGAATGCT GCAGTGATGC GCTACCCGGG    540
GTCGAAGTGG TCCCTCGCTC GGCAGATTGT CGCGGAATTC GATGACCACT ACCACTACGT    600
GGAACCGTTC TTCGGTTCGG GGGCGGTGTT CTTCAGCAAG CCGCCGGTGC CGCACGAGAT    660
CCTCAACGAC ACCAACGGTC AGGTCGTGAA CCTGTTCCGG GTGCTTCGCG ATCGGACCGA    720
GGATCTGGTG TGGCAGCTTG AGGCGACGCC TTGGTCTCGG GACGAGTATG ACCGGTCGCA    780
CGTCCTGACC GGGGATGATG TCGAGGACGC CAGACGGTTC GTGGTTCGGT GCTGGCAGGC    840
GCACGCGAGC GACCTGGCGA AGAAGACTGG GTGGAAGACC CGCGGCGCGC AGCAGCGTGC    900
CGGCGGGATG TCGCTGCGGT GGCAGAAGGT GCCGGCGCAG CTGCGGGAGC TTGCCTGGCG    960
GCTGTTGGAT GCGGAAATCG AGAACCGTGA CGCGGTGCAA GTGATCCGCC GGCACAACGC   1020
CGAGAACGCT CTGATCTACG CAGACCCGCC GTATCTACAC AGCGTCCGCA CGCAGCGCAT   1080
GTACGGCGAG GAGATGACCG ACACCGAGCA CATCGCCCTG CTGGACGCGC TACTGGCCCA   1140
CAAGGGGCCG GTGGTGGTCA GCGGGTACGC CAACGACCTA TACGACACTG CGCTCGAGGG   1200
GTGGCGCAAG GTGACAATGA AGGCGCCGAA GGTCGAGAAG GGTGCCGCCC GTACTGAGGT   1260
GCTGTGGGTA AAGCGCTAGT TACGGTCGTC CCAACCGTGC GGCCAGACCT CGTTGAAGTA   1320
GTCACGGGCC CGGAGGATCG GTGACGCCAC CGGCGGCAGT TCCAGCGTGA ACGGCTCCGT   1380
CACCCAGTCC GCCCACCGCA ACAGCGGGTA GTACTTCAGC TGCCCGCCGG AATTCATGTA   1440
GCACTGCCAC AACCGATGCC GTCGGCCGCC GTCATCGATA TACCCGTTCA GCGAAGCACC   1500
CTCGTGCAGC CACTCCACCT CGCCCACCGG GTTCGCGATC TGCAAGTCCA GGGGAAGCA   1560
GAGCAGCTGA AACTGCGTCC ATGACGGATT GTGGGCCAAC ACCGAGTACT TACTCGCGGG   1620
CAGGTCGAGT TGATGGGTGT CGGCGGTGGC GTCGTGCCAA CCGGTAACCA GACGCACGAT   1680
CGCAGGGCCA GCAAGACCGG GCTCGGTCGC CCAATTGATC TGCTGCGCCA GCAGCGCCTG   1740
GCGGAACTGG GCGGCGGAGT TAGACAGCTC CATGAAACTC GACGCATGCT TCGCCGGAGG   1800
TGTCGTGGCC ATTTTGCAGG AGATCCCGAA CGACTTATCG CCGTCGACGG GCACGATGAC   1860
GTCGAAGACG CCCTTGTTCT CCGGAGCTGA CGCATGCAGC ACGGCGGCGA GACCACGCTC   1920
GTAGTCGCGG AAGCCTGGCA TTGTGCCGCC ATTGGGGCGG ACAACCTGAC CGGATCCGTC   1980
TCGGAACGAG CTCAATACCA GCCGGAGGAC CTCCAGCTCG ACATCGTCGA GCGGCCGGTC   2040
ACGAAACGCG TAATCCACCC GCACATCGTA GAAGCCAACA AACAGTCGCC AACGGTCATA   2100
GCGCCGTGTC GCGGTGTCGG TTGCCGGCTG GTTCGACATG GCTGTTTGCC AAGACGCGAC   2160
GTCACGCCGT CCGAGGGGGA AGGATGACGT GCATGGATGC GGCACTGTGG GGTCAGGTTG   2220
TCATCGCCGC TGTCGCTGTT TTCGGGTCGG TCCTTGGGTA CATGCTCTCC GGCCTCAATG   2280
ATGCGCGGCG TGACCGGCGT ACGACGCTTC GGGAGCGTGC AGCACGGCAC GAGGAACGCG   2340
ACGCGGAAGA CCGACGTGAG CGGCATGCGT TCCAACGTGC AACGCTGCTC GAGCTGCAGG   2400
ACGCCGTTCA ACTCATGGCT CGGCTGACAG GCCGAACGAT GCACTTCGAC CACATGCAGG   2460
CGCGAGAGGG CAAACAGACA CAGCTTCCAT CGCAGTACGA CGATGAGATG CACGCAAACG   2520
GGGTCGATGT CATCCGTTTT CGGAACCGGC TCCTCGACGA CGACCTCCGT CGGTCGATCG   2580
CGGTGTTCGA ATCGCAGTGC GACCAGGTGT CGAAGCTGCC GCTGCGGTAT CAGGGACATG   2640
TCGGCGAGGA AGCCGACGGT GTGGCGTTCG AGCTGATGCG GACATTCGGC GATCAAGTGT   2700
CAGTCGTTAT GGACGCCGTC GGAGTAGCGC TGCGCCTAAA CCTCAGCACC CCTCCCCCCT   2760
TCGCCACCTC GTCGTGACAC ACGCTCGTGG TGGTCGAGGT CACCGACGCC CATGCCCATG   2820
TCCACGAGCC ACCGCCTTAC TTCGCGGACA CTAAGTGGAT ACCGTCCGTC GGGCGCCCGA   2880
```

```
TGCTGGGATG  GTGGCAGTCC  GGTAGCCGGT  CCGCCAGCAA  GCCACGAAAT  GCCTGCGGG       2940

GCTTCGGACT  CCTTCGGCTC  TGCTCTGGAG  GGAAACCCTG  TCTCACATAG  GTGGTCCGCG      3000

GACTATCTCA  GTTCAGGCAC  GCTGTACGGA  CGCGTCCCAG  CGCAGGAAGG  CTGAGCCGGG      3060

CGCTAGTCGA  CGTGGCCAAA  TAACCTGTCC  AACTCCGTAT  TTCCGGACAG  GTTGTGTGGC      3120

AGTAGGACAA  GTTAGCCTGC  GGACGACAAC  AAACGTGTCG  ACTGCCAGCC  AACTTGTCCG      3180

AT                                                                          3182
```

( 2 ) INFORMATION FOR SEQ ID NO: 7:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) MOLECULE TYPE: other DNA (synthetic)

( x i ) SEQUENCE DESCRIPTION: SEQ ID NO: 7:

```
ATGGATTACG  CGTTTCGTGA  CCGGCCGCTC                                          30
```

( 2 ) INFORMATION FOR SEQ ID NO: 8:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) MOLECULE TYPE: other DNA (synthetic)

( x i ) SEQUENCE DESCRIPTION: SEQ ID NO: 8:

```
CTAGTTACGG  TCGTCCCAAC  CGTGCGGCCA                                          30
```